(12) United States Patent
Dieras et al.

(10) Patent No.: US 6,312,256 B1
(45) Date of Patent: Nov. 6, 2001

(54) DENTAL ULTRASOUND INSTRUMENT FOR TREATING PERIODONTAL POCKETS

(75) Inventors: Francis Dieras, Bordeaux; Edmond-Pierre Benque, Toulouse, both of (FR)

(73) Assignee: Satelec SA, Merignac (FR)

( * ) Notice: Subject to any disclaimer, the term of this patent is extended or adjusted under 35 U.S.C. 154(b) by 0 days.

(21) Appl. No.: 09/600,251

(22) PCT Filed: Jan. 13, 1999

(86) PCT No.: PCT/FR99/00049

§ 371 Date: Jul. 13, 2000

§ 102(e) Date: Jul. 13, 2000

(87) PCT Pub. No.: WO99/35993

PCT Pub. Date: Jul. 22, 1999

(30) Foreign Application Priority Data

Jan. 13, 1998 (FR) .................................................. 98/00239

(51) Int. Cl.[7] .............................. A61C 1/07; A61C 3/03; A61C 3/08
(52) U.S. Cl. ............................................. 433/119; 423/118
(58) Field of Search .................................. 433/118, 119, 433/141, 142, 143, 144

(56) References Cited

U.S. PATENT DOCUMENTS

| | | | | |
|---|---|---|---|---|
| D. 261,932 | * | 11/1981 | Bussiere ........................... | 433/119 X |
| 2,990,616 | * | 7/1961 | Balamuth et al. ................... | 433/119 |
| 3,930,173 | * | 12/1975 | Banko .............................. | 433/119 X |
| 4,332,558 | * | 6/1982 | Lustig ............................. | 433/119 X |
| 5,531,597 | * | 7/1996 | Foulkes et al. ..................... | 433/119 |

\* cited by examiner

Primary Examiner—Nicholas D. Lucchesi
(74) Attorney, Agent, or Firm—Young & Thompson

(57) ABSTRACT

A dental instrument adapted to be fixed to a hand piece suitable for communicating ultrasound waves to the dental instrument, includes at least one arm ending in an active extremity that has two longitudinal concavities in opposing surfaces.

12 Claims, 2 Drawing Sheets

DENTAL ULTRASOUND INSTRUMENT FOR TREATING PERIODONTAL POCKETS

BACKGROUND OF THE INVENTION

The present invention relates to a dental ultrasound instrument and more particularly an instrument for treating the periodontal pockets which are characteristic of an infection of the periodontium.

In effect, it is known that, although tartar is not a pathogenic product per se, it nonetheless constitutes, by reason of its alveolar porous constitution, a support capable of receiving and promoting the development of microbial fauna.

When tartar is deposited on the supergingival part of the tooth, viz. on the enamel thereof, it may easily be removed with the aid of a manual instrument or an ultrasound instrument moved.

The same does not apply when it is deposited on the subgingival part of the tooth, namely on the cementum thereof, due to the considerable roughness of the latter. In the latter case, the subgingival tartar will promote the formation of dental plaque which in the long run will lead to a disease of the periodontium, or periodontitis, which manifests itself by the presence of the periodontal pocket mentioned above. In the absence of treatment, periodontitis will lead to a loss of the attachment of the tooth and to a resorption of the alveolar bone. It is therefore essential to treat the periodontal pocket.

The purpose of the treatment which is carried out is conventionally to clean the surface of the root of the tooth in order to eliminate the harmful deposits therefrom, and then to polish it in order to obtain a smooth surface. Such an operation, called radicular surfacing, is effected "blind" for periodontal pockets of small dimensions. In the contrary case, a gingival flap is made, which allows direct access to the radicular surfaces affected by the disease.

Blind radicular surfacing requires particularly adapted instrumentation due, on the one hand, to the anatomical variety of the sites concerned and their difficult access and, on the other hand, due to the fragility of the tissues encountered. Certain of the instruments used to that end are of diverse forms and are used either in traction or in thrust. Among the instruments used in traction, the instruments of type "Crane Kaplan No. 6", "Goldman Fox No. 1" or "Mac Call" will be retained in particular. Certain instruments of the type operating in thrust are constituted by chisels presenting a straight, flat and bevelled cutting edge and a continuous blade (Zerfin 6 chisel).

All these instruments comprise contusive zones in order to allow engagement on the tartar which, due to the rough nature of the cementum, forms part thereof.

Among the instruments most used for radicular surfacing operations, curettes will be retained, and in particular so-called "Gracey" curettes which, by reason of their semicircular cross-section, may be easily inserted in the majority of the zones of the dentition in order to effect both the scraping operation with their sharp zone and the polishing operation with their rounded zone. This type of instrument presents the drawback of requiring numerous periodic sharpenings. Moreover, when the contusive part of the blade encounters a piece of tartar, it is necessary to apply a high force to the instrument, which may prove dangerous for the surrounding tissues.

Furthermore, the time necessary for carrying out manual treatment by means of the above-mentioned instruments may prove to be very long and it is for this reason that it has been proposed to render this operational technique mechanical by activating these instruments by means of ultrasound generator devices, as proposed in particular in a Canadian Patent No. 597 313.

Another drawback of the instruments mentioned hereinabove is that, in order to effect an operation of radicular surfacing on the same tooth, the practitioner is obliged to change instruments several times during operation, which constitutes both a hindrance and a loss of time for him.

Although the ultrasound instruments avoid the practitioner tiring greatly and allow him to save considerable time, they nonetheless present a certain number of drawbacks which are essentially due to the fact that the instruments of this type do not take into account the most recent scientific data on the subject.

In effect, it is known that the operation of radicular surfacing mentioned hereinabove consists in removing the cementum and the dentine from the diseased places in order to eliminate those parts thereof containing microbial fauna. Unfortunately, this operation also has the effect of inducing phenomena of hypersensitivity or of ascending pulpitis and of subsequently promoting the adhesion of bacteria on the places thus treated.

At the present time, the so-called operations of debridement of the periodontal pocket seem to be preferred to the operation of radicular surfacing. Such an operation, unlike the latter one, respects the whole of the cementum and the dentine.

It consists in opening the periodontal pocket, cleaning the root and in effecting mechanical excision of the irritants of the dental and radicular surface. Debridement goes as far as the adjacent non-pathological tissues, upsets the microbial organization established, resulting in a non-inflammatory state of the tissues. Debridement makes it possible to achieve a total scarring of the lesion by detoxification of the tissues and cemento-genesis.

Such an operation requires a non-contusive instrument for effecting cleaning and smoothing both rapidly and non-aggressively, contrary to the effect of scraping/polishing obtained with conventional instruments, including those animated by ultrasounds.

Furthermore, it is known that ultrasound instruments used in dentistry are capable of producing an effect of cavitation which is advantageously used for eliminating the tartar which is deposited on the supergingival surfaces of the tooth. The instruments of the prior state of the art, which were described hereinabove, prove to be incapable, by the sole effect of cavitation that they create, of eliminating from the root of the tooth the subgingival concretions which adhere thereto. This is why these instruments present a contusive part whose effects are intended to be added to that of cavitation in order to "machine" to some extent the concretions to be eliminated.

SUMMARY OF THE INVENTION

U.S. Pat. No. 3,645,255 discloses a dental handpiece animated by an ultrasound transducer, the extremity of this handpiece being supplied with irrigation liquid, this handpiece ending in a pointed active extremity.

PCT WO 99/00631 also discloses a handpiece of which the tool is moved by an ultrasound transducer which comprises a hollow zone supplied with irrigation liquid, the active extremity of this instrument being rounded and the lateral walls limiting the hollow zone having a contusive upper part.

The present invention has for its object to propose a dental instrument for effecting the operation of debridement of a periodontal pocket by means of ultrasounds, calling upon a phenomenon of amplified cavitation, this avoiding for the practitioner any risk of deterioration of the non-pathological cementum or dentine of the tooth.

It has been observed that, under certain conditions of particular shapes of an instrument, the phenomenon of cavitation produced was sufficient to allow the elimination of said concretions. It has also been observed that this effect could be obtained with the aid of instruments not presenting any contusive part. Under these conditions, the practitioner is guaranteed that he does not harm the integrity of the root of the tooth.

In effect, it has been observed that, by creating an acoustic chamber between the active extremity of the instrument and the concretion deposited on the surface of the tooth, which concretion is to be eliminated, the phenomenon of cavitation was amplified to such a point that its level thus obtained allowed said concretion to be rapidly destroyed.

The present invention thus has for its object a dental instrument which can be fixed to a handpiece suitable for communicating ultrasound vibrations thereto, of the type particularly intended for treating periodontal pockets and which is formed by at least one arm ending in an active extremity, characterized in that:

the active extremity comprises at least one face provided with a hollow zone extending along the longitudinal axis thereof, this hollow zone is adapted to receive a supply of irrigation liquid, said active extremity does not present any contusive zone.

The means for supplying the hollow zone with irrigation liquid will preferably form an integral part of the instrument.

The effect of cavitation connected with the formation of an acoustic chamber is increased further insofar as there is provided on the opposite face of the instrument a second hollow zone, preferably symmetrical to the first with respect to a plane, itself supplied with irrigation liquid. This arrangement not only increases the effect of cavitation on the face of the tooth but also allows the irrigation liquid projected from the second hollow zone of the instrument, to be propelled by the vibrations of the latter on the gum of the tooth, thus cleaning the latter. It will then be noted that such an instrument performs two functions simultaneously during operation, namely the breaking off of the concretions by effect of amplified cavitation and the cleaning of the sulcus, thus saving the practitioner time, enabling him to pass in interproximal from one periodontal pocket to another.

In an embodiment of the invention, the hollow zone will have a parabolic cross-section such that its focus will be located substantially at a distance from the bottom thereof corresponding to the location of the surface of the concretion during treatment.

It has been observed that, by giving the active extremity of the instrument (i.e. that part thereof likely to come into contact with the tooth during treatment), a determined specific shape, it was possible to ensure a complete treatment of debridement of the periodontal pocket of a tooth on all the faces thereof, without the practitioner having to proceed with a change of instrument during operation. In fact, by giving the instrument this determined specific shape, it is even possible, with one instrument, to effect the above-mentioned operation on all the patient's teeth. Under these conditions, not only the practitioner benefits from a greater rapidity of treatment and greater work comfort, but he also makes substantial savings, insofar as one instrument replaces the various instruments necessary up to the present time. The active extremity will thus preferably present at least one face in the overall shape of an isosceles trapezium of which the axis of symmetry merges with that of the arm to which it is connected and of which the small base forms the anterior part.

The instrument according to the invention further improves safety for the patient insofar as it does not comprise any contusive edge.

Various forms of embodiment of the present invention will be described hereinafter by way of non-limiting examples, with reference to the accompanying drawings, in which:

DESCRIPTION OF THE PREFERRED EMBODIMENTS

Figure 1:
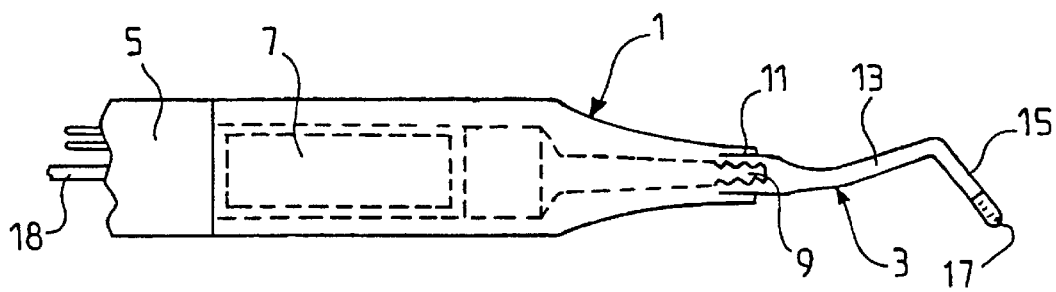
FIG. 1 is a plan view of a surgical assembly comprising an instrument according to the invention.

The surgical assembly shown in FIG. 1 is essentially composed of a handpiece 1 and an instrument 3. The handpiece 1 is constituted by a cylindrical casing 5 which contains a piezo-electric transducer 7 connected to electricity-supply means (not shown in the drawing). The transducer 7 terminates in a threaded endpiece 9 on which is screwed the bushing 11 of the instrument 3.

Figure 2:
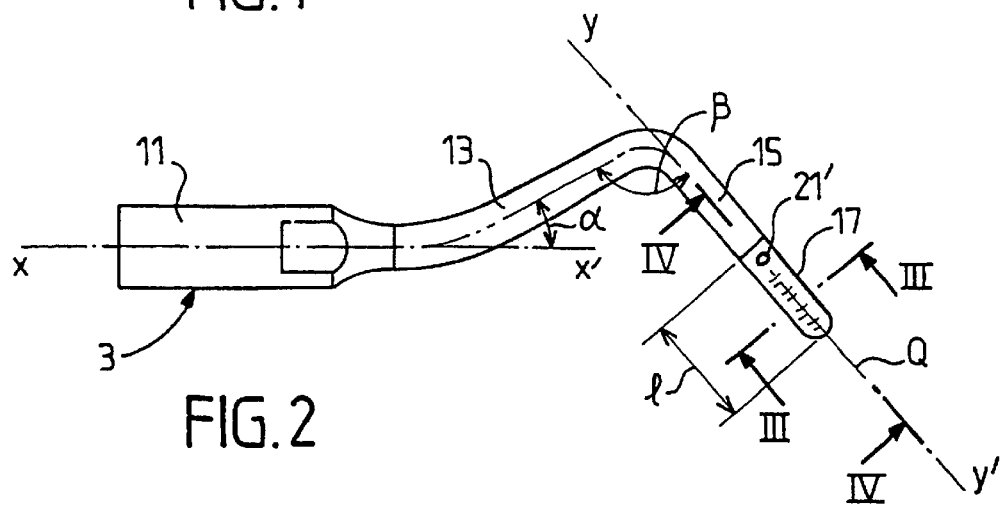
FIG. 2 is a plan view of an example of a dental instrument according to the invention.

The latter, which is shown in greater detail in FIG. 2, is composed of the cylindrical bushing 11 which extends in a cylindrical arm 13 of smaller diameter and whose longitudinal axis forms an angle $\alpha$ of about 40° with the longitudinal axis xx' of the bushing 11. This first arm 13 extends in a second arm 15, substantially of the same length, which is bent in opposite direction and which forms an angle $\beta$ of about 90° with the first arm 13. The second arm 15 ends in an active extremity 17, i.e. a part of which the various faces can be placed in contact with the different zones of the tooth to be treated.

Figure 3:
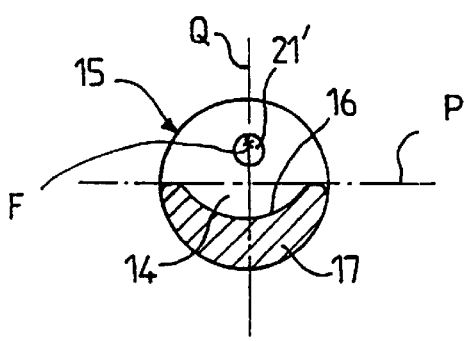
FIG. 3 is a view in cross-section on a larger scale of the active extremity of the dental instrument shown in FIG. 2, along line III—III thereof.
Figure 4:
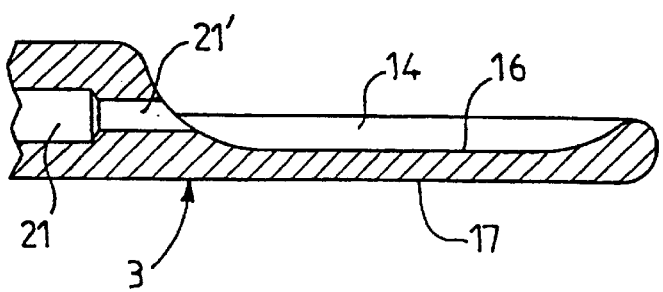
FIG. 4 is a view in longitudinal section on a larger scale of the active extremity of the dental instrument shown in FIG. 2, along line IV—IV thereof.

The active extremity 17 is obtained by machining the arm 15. As shown in FIG. 3, it presents a cross-section in the form of a half-moon of which the angular parts are rounded, thus forming a hollow zone 14. The plane of symmetry Q of the active extremity 17 is perpendicular to the plane P formed by the two arms 13 and 15. The inner face 16 of the hollow zone 14 is substantially in the form of an arc of circle.

In an embodiment of the invention, this face 16 may present a parabolic shape, the focus F of the parabola then lying at a distance therefrom such that, in position of use, it lies on the surface of the concretion 19 which it is desired to eliminate.

It is known that the phenomenon of cavitation can, of course, occur only in the presence of a liquid. This may be supplied by outside means, but it will preferably be supplied by the instrument itself. To that end, the handpiece 1 presents liquid-supply means 18 which are connected via communication means (not shown in the drawing) with a supply channel 21 provided at the centre of the instrument 3 and which opens out in the hollow zone 14 thereof.

Figure 5:
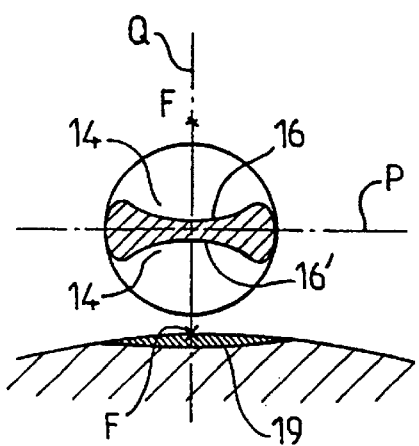
FIG. 5 is a view in cross-section of a variant embodiment of the active extremity of an instrument according to the invention.
Figure 6:
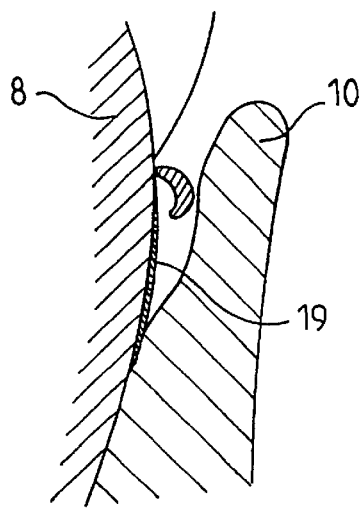
FIG. 6 is a schematic view in section of an instrument according to the invention in work position between the cementum and the gum of a tooth.
Figure 7:
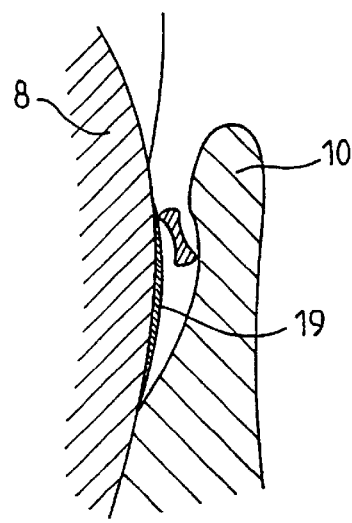
FIG. 7 is a schematic view in section of a variant embodiment of an instrument according to the invention in work position between the cementum and the gum of a tooth.

It is observed that the efficiency of the amplified cavitation was improved when the instrument 3 presented two hollow zones 14, preferably identical and symmetrical with respect to plane P. FIG. 5 thus shows an instrument of the type shown in FIG. 3 but which, in addition, is symmetrical with respect to the plane P formed by the arms 13 and 15. Such an arrangement, as shown in FIG. 7, allows the practitioner, while attacking the concretions 19 with his instrument, disposing the latter so that one of the hollow parts is directed towards the concretion in order to form an acoustic chamber generating an amplified cavitation, to clean the gum 10 with the opposite face.

Figure 8:
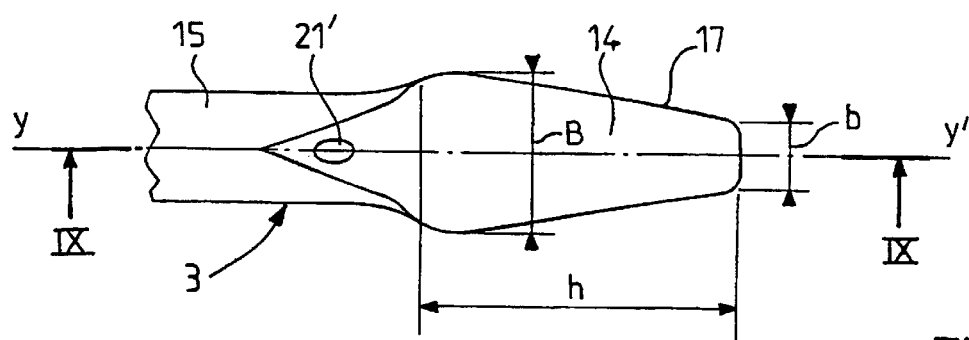
FIG. 8 is a partial plan view of a variant embodiment of the active extremity of an instrument according to the invention.
Figure 9:
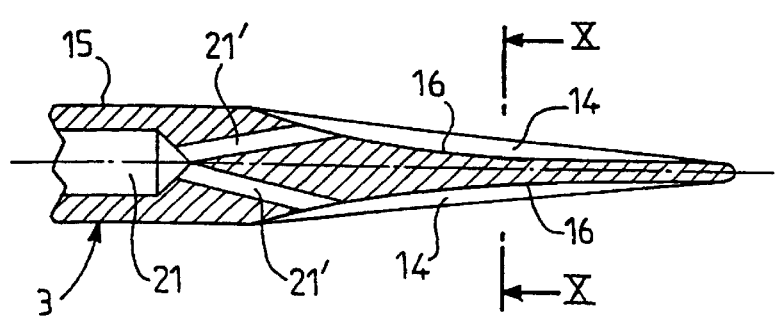
FIG. 9 is a view in longitudinal section of the instrument shown in FIG. 8 along line IX—IX thereof.
Figure 10:
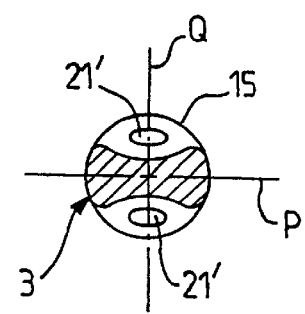
FIG. 10 is a view in cross-section of the instrument shown in FIG. 8 along line X—X thereof.

In a preferred embodiment of the invention shown in FIGS. 8 to 10, and in order to give a more general function to the instrument, i.e. allow it to effect not only a complete treatment of a given tooth 8, but to carry out this treatment on all the patient's teeth, a specific shape of its active extremity 17 has been designed which, overall, i.e. a in view along plane P of the two arms 13 and 15, is that of an isosceles trapezium of which the small base and the large base present rounded angles. The large base B of the trapezium is slightly larger than the diameter of the second arm 15 and is of the order of 2.5 mm, its height h is of the order of 5 mm and its small base b is of the order of 1 mm. The two hollow parts 14 of the instrument are symmetrical with respect to the plane P defined by its two arms 13 and 15 and all the zones of the active extremity of the instrument 3 are rounded in order that no contusive edge exists.

The instrument is traversed by a supply channel 21 which, near the hollow zones 14 of the active extremity 17, separates into two secondary channels 21' of smaller diameter and which are inclined with respect to plane P, and which open out respectively in the upstream part of each hollow zone 14, these channels supplying to the latter the liquid necessary for the formation of the phenomenon of cavitation.

What is claimed is:

1. A dental instrument adapted to be fixed to a hand piece that communicates ultrasound vibrations to the dental instrument, the dental instrument comprising:

an arm ending in an active extremity;

two longitudinal concavities in opposite surfaces of said active extremity, said two concavities being symmetrical about a flat plane between them; and an opening for expelling an irrigating liquid into at least one of said concavities.

2. The dental instrument of claim 1, wherein each of said longitudinal concavities has a focus that is beyond a circumference of said arm.

3. The dental instrument of claim 1, wherein said active extremity comprises an isosceles trapezium with a small base at a distal tip of said active extremity and a large base between said distal tip and said opening.

4. The dental instrument of claim 1, wherein said arm comprises two non-parallel segments whose longitudinal axes lie in the flat plane.

5. The dental instrument of claim 4, wherein the longitudinal axes of said two segments have an angle of about 90° between them.

6. The dental instrument of claim 5, wherein each of said concavities has one said opening therein.

7. A dental instrument adapted to be fixed to a hand piece that communicates ultrasound vibrations to the dental instrument, the dental instrument comprising:

an arm with a longitudinally extended active end that is a flat plate whose lateral peripheries are increasingly elevated away from a longitudinal centerline of said plate on both opposing surfaces of said plate so that each of the opposing surfaces has a longitudinal concavity therein; and an opening for expelling an irrigating liquid into at least one of said concavities.

8. The dental instrument of claim 7, wherein said flat plate is trapezoidal.

9. The dental instrument of claim 7, wherein a thickness of said flat plate increases away from a distal tip of said active end.

10. The dental instrument of claim 7, wherein each of said longitudinal concavities has a focus that is beyond a circumference of said arm.

11. The dental instrument of claim 7, wherein said arm comprises two non-parallel segments whose longitudinal axes lie in a plane of said flat plate.

12. The dental instrument of claim 7, wherein each of said concavities has one said opening therein.

* * * * *